United States Patent
Sefton

(10) Patent No.: US 8,071,578 B2
(45) Date of Patent: *Dec. 6, 2011

(54) TAZAROTENE AND CORTICOSTEROID TREATMENT FOR PSORIASIS

(75) Inventor: John Sefton, Trabuco Canyon, CA (US)

(73) Assignee: Allergan, Inc., Irvine, CA (US)

( * ) Notice: Subject to any disclaimer, the term of this patent is extended or adjusted under 35 U.S.C. 154(b) by 974 days.

This patent is subject to a terminal disclaimer.

(21) Appl. No.: 10/820,298

(22) Filed: Apr. 7, 2004

(65) Prior Publication Data

US 2004/0192662 A1    Sep. 30, 2004

Related U.S. Application Data

(63) Continuation of application No. 09/367,712, filed as application No. PCT/US98/03355 on Feb. 20, 1998, now Pat. No. 6,974,807.

(60) Provisional application No. 60/039,151, filed on Feb. 20, 1997.

(51) Int. Cl.
*A61K 31/573* (2006.01)

(52) U.S. Cl. ...................................................... 514/171
(58) Field of Classification Search .................. 514/171
See application file for complete search history.

(56) References Cited

U.S. PATENT DOCUMENTS

| | | | | | |
|---|---|---|---|---|---|
| 4,775,529 | A | * | 10/1988 | Sequeira et al. | 514/171 |
| 5,236,906 | A | * | 8/1993 | Yamamoto | 514/171 |
| 5,650,279 | A | * | 7/1997 | Nagpal et al. | 435/6 |
| 5,874,074 | A | * | 2/1999 | Smith | 424/78.02 |
| 5,914,334 | A | * | 6/1999 | Charu | 514/337 |

OTHER PUBLICATIONS

Schwartz, Biological Abstracts, vol. 10, Philadelphia, PA, US; abstract No. 981998 & Journal of Investigative Dermatology, 102 (2). 1994. 241-246.

* cited by examiner

*Primary Examiner* — Barbara P Badio
(74) *Attorney, Agent, or Firm* — Ted A. Chan; Debra Condino

(57) ABSTRACT

The present invention provides a method for treating proliferative skin diseases comprising the administration of an effective amount of tazarotene and an effective amount of a corticosteroid. This invention is especially useful for treating psoriasis.

7 Claims, 2 Drawing Sheets

TAZAROTENE AND CORTICOSTEROID TREATMENT FOR PSORIASIS

CROSS REFERENCE TO RELATED APPLICATIONS

This application is a continuation application under 37 CFR 1.53(b) and 1.78(a), of and claims priority to prior parent U.S. patent application Ser. No. 09/367,712, filed Aug. 18, 1999, now U.S. Pat. No. 6,974,807, which is a national stage application of PCT/US98/03355, filed Feb. 20, 1998, which claimed priority to U.S. Provisional Patent Application 60/039,151, filed on Feb. 20, 1997 for TAZAROTENE AND CORTICOSTEROID TREATMENT FOR PSORIASIS. The disclosures of all of these priority documents are expressly incorporated by reference herein.

BACKGROUND OF THE INVENTION

1. Field of the Invention

This invention relates to pharmaceutical compositions for application to the skin and to a method for the treatment of proliferating skin diseases. The composition may be applied topically. The treatment can be either therapeutic or prophylactic.

2. Description of Related Art

Proliferative skin diseases are widespread throughout the world and afflict millions of humans and their domesticated animals. This invention provides a method for treatment of such diseases. As used hereinafter in this specification and in the claims, the expression "proliferative skin diseases" means benign and malignant proliferative skin diseases which are characterized by accelerated cell division in the epidermis, dermis or appendages thereto, associated with incomplete tissue differentiation. Such diseases include: psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrhic dermatitis in humans and atopic dermatitis in domesticated animals.

Heretofore, proliferative skin diseases have been generally accepted by mankind as an ongoing evil having degrees of severity variable with inherited skin traits and external factors but always have been recognized as unsightly, painful, morbid diseases. Over the history of mankind innumerable medicines and treatments have been proposed, tried and used with varying degrees of success.

Treatments which are prescribed and used for the treatment of proliferative skin diseases include the following:

(1) topical applications, e.g. coal tar derivatives, 5-fluorouracil, vitamin A acid, glucocorticoids in high dosage, bath oils and non-specific emollient creams and ointments;

(2) systemic administration, e.g. glucocorticoids and classic anti-cancer agents, for example, methothrexate, hydroxyurea, azaribine, cyclophosphamide; and (3) physical modalities, e.g. ultra violet light, x-radiation, and, in severe cases, surgery.

While these treatments provide, in certain cases some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocorticoids, acute bone marrow suppression, cirrhosis of the liver resulting from the protracted use of methothrexate which may lead to death of the patient, and the causation of cancer by the application of anti-cancer drugs, x-radiation, or ultra violet rays.

Recently, a new compound has been approved by the Food and Drug Administration for the treatment of psoriasis and acne. Tazarotene. Tazarotene is available as Tazorac® 0.1% and Tazorac® 0.05% topical gel from Allergan, Inc. of Irvine, Calif.

BRIEF SUMMARY OF THE INVENTION

The present invention relates to a method of treating psoriasis in humans with tazarotene, preferably a gel comprising 0.1%, tazarotene by weight, and a corticosteroid, preferably a cream. The tazarotene gel may be administered once daily in the evening and the corticosteroid cream may be administered to the subject once daily in the morning, or the gel and cream may be administered on alternate days. The tazarotene gel is disclosed in U.S. patent application Ser. No. 623,184, which is entitled "Stable Gel Formulation for Topical Treatment of Skin Conditions", which was filed on Mar. 28, 1996, in the name of Prakash Charu and is hereby incorporated by reference in its entirety.

In one aspect of the invention, the corticosteroid may be Synalar® cream (0.01% fluocinolone acetonide), Elocon® cream (0.1% mometasone furoate) or Lidex® cream (0.05% fluocinonide), i.e. a low-potency, mid-potency and high-potency corticosteroid, respectively.

In another aspect of the invention, the corticosteroid may be fluocinonide 0.05% ointment, Lidex®, a high potency steroid, mometasone fuoate 0.1% ointment, Elocon®, a high potency steroid, diflorasone diacetate 0.05% ointment, Maxiflor®, a high potency steroid, fluticasone propionate 0.005% ointment, Cultivate®, a mid-potency steroid, betamethasone dipropionate 0.05% cream, Diprosone®, a mid-potency steroid, diflorasone diacetate 0.05% cream, Maxiflor®, a mid-potency steroid, clobetasol propionate 0.05% ointment, Temovate®, a super-potency steroid, betamethasone valerate 0.1% lotion, Valisone®, a mid-potency steroid.

DETAILED DESCRIPTION OF THE INVENTION

Figure 1:
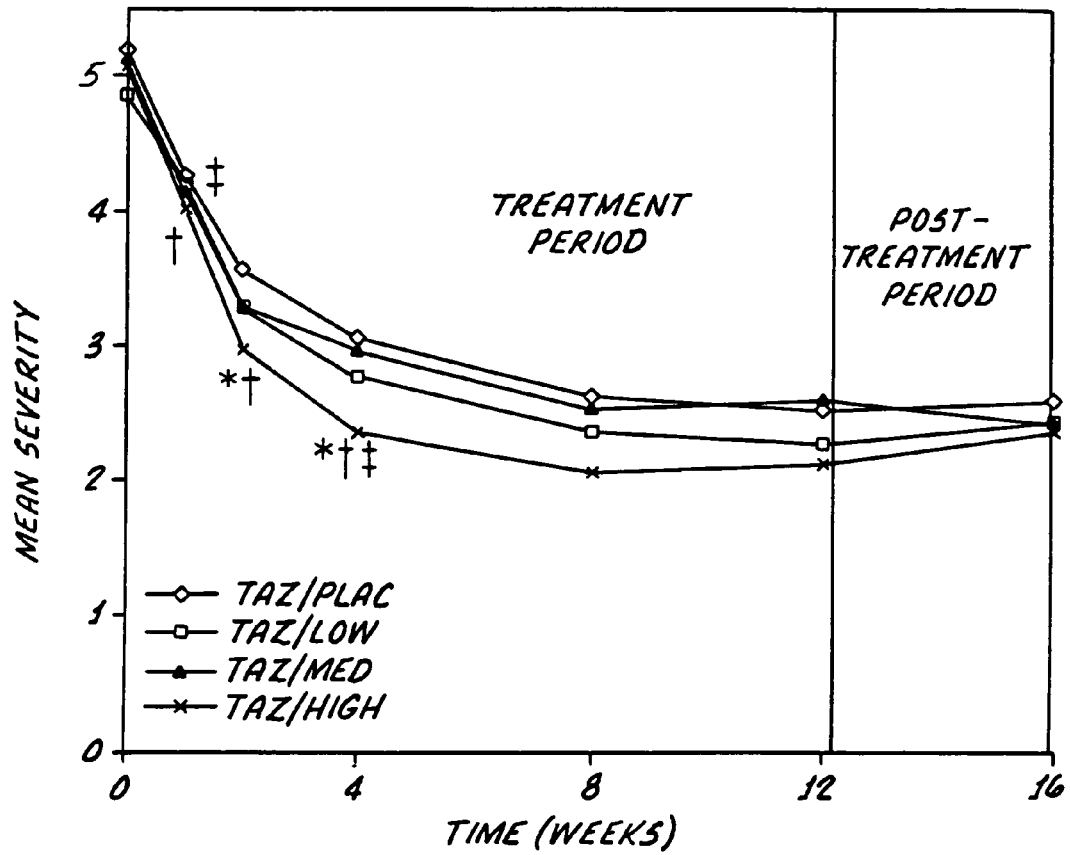
FIG. 1 is a graph comparing the reduction in plaque elevation over a 12 week treatment period with tazarotene in combination with placebo, high-potency corticosteroid, mid-potency corticosteroid and low-potency corticosteroid.

In accordance with this invention it has been found that proliferative skin diseases are alleviated, that is, the symptoms of the disease are noticeably improved or become undetectable, by the treatment of the afflicted patient, or animal, with the pharmaceutical compounds described in detail, hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and the claims hereof, psoriasis is alleviated when a scale-free psoriasis lesion is noticeably decreased in thickness, or noticeably but incompletely cleared or completely cleared.

The compositions utilized in the method of this invention may be applied topically.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petroleum, lanolin, polyethylene glycols, as well as mixtures thereof. Topical application with occlusion of an area larger than the medicated area may produce improved results relative to non-occluded topical applications.

The percentage by w/w of the active ingredient, i.e. the corticosteroid herein utilized ranges from about 0.001% to about 1% of the pharmaceutical preparation, preferably from about 0.005% to about 0.1%, by weight.

The percentage by w/w of the active ingredient, i.e. tazarotene herein utilized ranges from about 0.01% to about 15% of the pharmaceutical preparation, preferably from about 0.1% to about 2% and in these preparations the aforesaid pharmaceutical carrier for topical application constitutes a major amount of the said preparation.

Preferably tazarotene is utilized as a stable gel formulation for topical treatment of skin conditions in humans, said stable gel formulation comprising: Ethyl-[2-(4,4-dimethylthiochroman-6-yl)ethynyl]nicotinate in a plurality of nonaqueous vehicles for both solubilizing tazarotene and forming a gel therewith, said nonaqueous vehicles enabling topical application of the gel to a skin condition, said plurality of vehicles each being present in amounts, and in combination, to control release of tazarotene from the gel to the skin conditions. In the tazarotene formulation the vehicles are present in amounts selected to produce maximum release of the active agent, i.e. tazarotene, from the gel when all the vehicles are present therein. Preferably the formulation comprises three vehicles and more preferably the formulation comprises three vehicles which are used to both solubilize the active agent and form a gel.

The formulation preferably comprises the three vehicles, e.g. Polysorbate 40, Poloxamer 407 and Hexylene glycol. Polysorbate 40 is

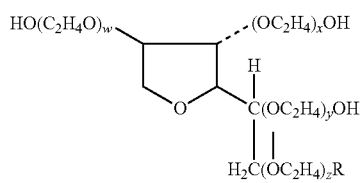

wherein the Sum of w, x, y, and z is 20 and R is $(C_{15}H_{31})COO$ and Poloxamer 407 is $HO(C_2H_4O)_a(C_3H_6O)_b(C_2H_4O)_aH$ having the following properties.

| USAN for Poloxamers | | | | | |
|---|---|---|---|---|---|
| Poloxamer | Physical Form | Average Molecular Weight | Average Values a | b | BASF Corp. Brand Name Pluronic |
| 124 | Liquid | 2090 to 2360 | 12 | 20 | L 44 |
| 188 | Solid | 7680 to 9510 | 80 | 27 | F 68 |
| 237 | Solid | 6840 to 8830 | 64 | 37 | F 87 |
| 338 | Solid | 12700 to 17400 | 141 | 44 | F 108 |
| 407 | Solid | 9840 to 14600 | 101 | 56 | F 127 |

More preferably, tazarotene is utilized as a stable gel formulation for topical treatment of psoriasis comprising an effective amount of Ethyl-6-[2-(4,4-dimethylthiochroman-6-yl)ethynyl]nicotinate in a pharmaceutical carrier comprising:
(a) water;
(b) edetate disodium;
(c) ascorbic acid;
(d) Carbomer 934P;
(e) Poloxamer 407;
(f) polyethylene glycol;
(g) Polysorbate 40;
(h) hexylene glycol;
(i) butylated hydroxytoluene;
(j) butylated hydroxyanisole;
(k) benzyl alcohol; and
(l) tromethamine.

The tazarotene formulation may comprise Polysorbate 40 in an amount up to about 0.4% by weight, Poloxamer 407 in an amount up to about 0.4% by weight, and hexylene glycol in an amount up to about 2% by weight or more preferably Polysorbate 40, in an amount of about 0.32% by weight, Poloxamer 407 in an amount of about 0.18% by weight, and hexylene glycol in an amount of about 2% by weight.

Most preferably, the tazarotene formulation comprises:

| INGREDIENT | FUNCTION | CONCENTRATION % W/W |
|---|---|---|
| tazarotene | Drug | 0.1 |
| purified water | Excipient | 49.25 |
| Edetate Disodium | Stabilizer | 0.05 |
| Ascorbic acid | Stabilizer | 0.05 |
| Carbomer 934P[1] | Thickening agent | 1.25 |
| Poloxamer 407 | Surfactant | 0.2 |
| PEG-400 | Co-solvent | 45.0 |
| Polysorbate 40 | Surfactant | 0.2 |
| Hexylene glycol | Co-solvent | 2.0 |
| Butylated hydroxytoluene | Stabilizer | 0.05 |
| Butylated hydroxyanisole | Stabilizer | 0.05 |
| Benzyl alcohol | Preservative | 1.0 |
| Triethanolamine/ Tromethamine | Neutralizer | 0.8 |

[1]Carbomer 934P [1975]. NF. The viscosity of a neutralized 0.5 percent aqueous dispersion of Carbomer 934P is between 29,400 and 39,400 centiposes. (1) Polymer of 2-propenoic acid, cross-linked with allyl ethers of sucrose or pentaerythritol; (2) Polymer of acrylic acid, cross-linked with allyl ethers of sucrose or pentaerythritol. Molecular weight is approximately 3,000,000.

The tazarotene formulation and the corticosteroid formulation, each, will be applied, topically, in an amount to achieve the maximum effect on alleviating the proliferative skin disease symptoms without causing an adverse reaction. Selection of such an amount of either formulation is well within the skill of the art.

Preferably, the tazarotene formulation is utilized to provide from about 0.5 to about 5 mg of tazarotene per $cm^2$ of affected skin, more preferably from about 1 to about 3 $mg/cm^2$, e.g. 2 $mg/cm^2$.

The method of this invention also employs a corticosteroid. The expression "corticosteroid" refers to a naturally occurring product of the adrenal cortex, or a synthetic analog thereof possessing anti-inflammatory activity and minimal or no mineralocorticoid activity or sex steroid activity. The corticosteroids include glucocorticoids. Of the natural glucocorticoids, one may use for example, hydrocortisone or the synthetic glucocorticoids such as methyl prednisolone acetate (Prednisone) or triamcinolone for topical therapy. The corticosteroids are preferably employed in amounts of from 0.5 to 5 mg per $cm^2$ of affected skin, more preferably from about 1 to 3 $mg/cm^2$, e.g. 2 $mg/cm^2$.

The treatment period may be 12 weeks with a 4 week follow-up period. The subjects are evaluated for plaque elevation, scaling and erythema with a successful treatment defined as about 50% improvement or better. During the treatment period, tazarotene in combination with the mid- or high-potency corticosteroid produced significantly better results than treatment with tazarotene in combination with placebo in reducing plaque elevation, scaling, erythema and overall severity. During the 4 week post-treatment period, the results with tazarotene plus mid- or high-potency corticosteroid were equal to or better than tazarotene plus placebo or tazarotene plus low-potency corticosteroid.

The most common adverse events resulting from the treatment were burning, pruritus and erythema; however there was a lower incidence of such adverse events in patients treated with tazarotene plus the medium- or high-potency corticosteroid.

Thus, treating psoriasis in humans with a combination of tazarotene and a mid-potency or high-potency corticosteroid is more effective than a combination of tazarotene and low-potency or placebo and results in a lower incidence of adverse events such as burning pruritis and erythema.

The invention is further illustrated by the following examples which are illustrative of various aspects of the invention, and are not intended as limiting the scope of the invention as defined by the appended claims.

EXAMPLE 1

The study reported here utilizes a combination regimen that alternates between tazarotene 0.1% gel and a corticosteroid or placebo cream every evening. The aim of the study was to determine whether such alternating therapy may offer clinical benefits by maximizing the therapeutic benefits of both drugs, while also minimizing corticosteroid use and thus reducing the potential for adverse corticosteroid-induced effects.

This study was a multicenter, investigator-masked, parallel-group study, enrolling 398 patients with stable plaque psoriasis. Topical applications of tazarotene 0.1% gel, were administered every other evening, and one of the following creams administered on alternate evenings): placebo; low-potency corticosteroid (hydrocortisone acetate 1%); medium-potency corticosteroid (alclometasone dipropionate 0.05%); or high-potency corticosteroid (betamethasone valerate 0.1%).

The study required a 12-week treatment period plus a 4-week follow-up phase. The patient demographics included 388 patients (231 male and 157 female) with evaluable data, mean age of 46.7 years (range: 21-88 years) and a mean duration of psoriasis of 17.39 years.

All treatment groups achieved clinically significant reductions in plaque elevation at all treatment and post-treatment visits, with the tazarotene/high-potency combination taz/high group achieving consistently greater reductions than the other treatments throughout the study. At week 4, these reductions were significantly greater than those in all the other treatment groups. The taz/high also achieved clinically significant reductions in plaque elevation more rapidly than the other treatments, i.e. in two weeks compared with four weeks in all the other groups. (See the results set forth in FIG. 1.)

Treatment success was defined as a moderate, marked, almost clear or completely cleared response ($\geq 50\%$ global clinical improvement). All tazarotene/corticosteroid treatment groups achieved treatment success rates of >50% within 4 weeks. However, the taz/high combination achieved significantly greater treatment success rates than the tazarotene/placebo (taz/plac) and tazarotene/medium-potency corticosteroid (taz/med) combinations throughout the 12-week treatment period. Peak treatment success rates ranged from 56% (for patients treated with taz/plac at Week 8) to 77% (for taz/high at Week 8).

Figure 2:
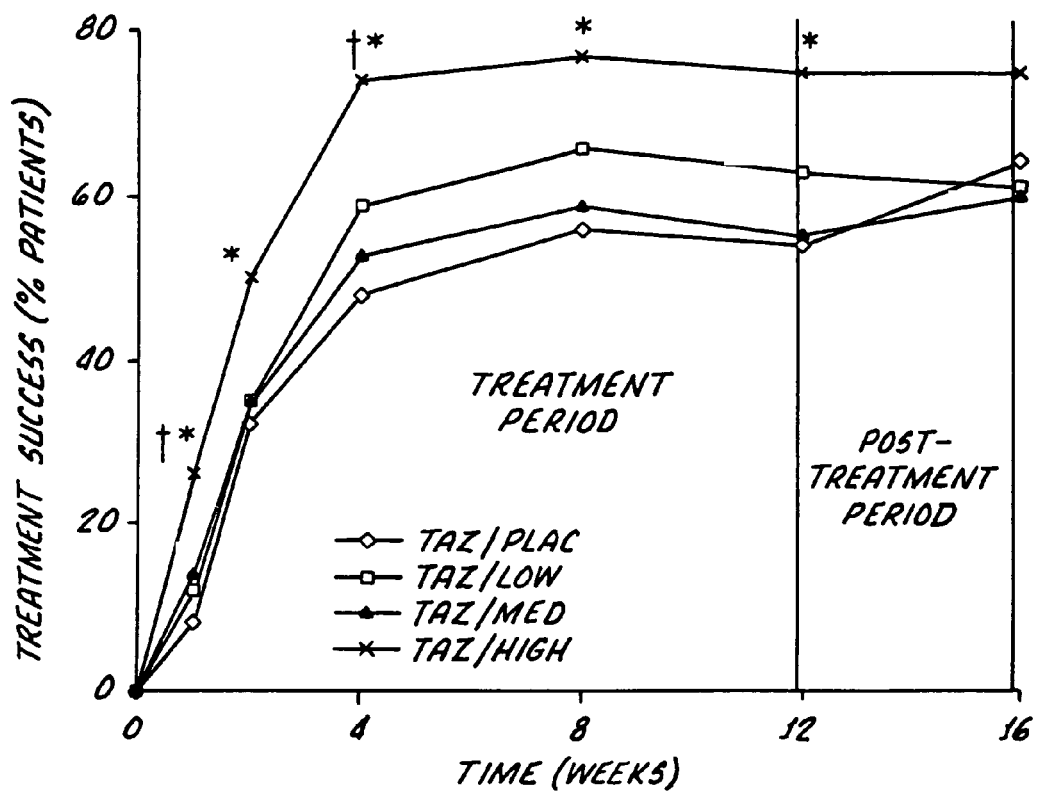
FIG. 2 shows the treatment success with the combination therapies of FIG. 1.

During the 4-week follow-up period, all groups retained $\geq 60\%$ global clinical improvements in psoriasis, with treatment success rates ranging from 60% (for taz/med) to 75% (for taz/high) at study Week 16. These improvements were statistically and clinically significant compared with the pretreatment levels and there were no significant differences between the groups at the end of the follow-up period. (See FIG. 2.)

Week 12, the probability of patients being considered a treatment success at any study visit was 77% in the taz/high group. In the other groups the treatment success was 56 to 61%.

The taz/high combination also achieved initial treatment success significantly faster than any of the other combinations. The median time to treatment success was 2 weeks in the taz/high group, compared with 4 weeks in each of the other groups.

All treatment groups achieved clinically significant reductions in scaling during the treatment period, and the taz/high combination was consistently the most efficacious treatment throughout the 12-week treatment period. The reductions in scaling achieved in all groups by the end of the treatment period were generally maintained during the 4-week follow up period.

All treatment groups achieved statistically significant reductions in erythema during the treatment period and, once again, the taz/high combination was the most efficacious treatment. During the follow-up period, all groups retained significant reductions in erythema compared with baseline levels, and these reductions were clinically significant in the taz/high, taz/med, and taz/plac groups.

The overall incidence of adverse events that were possibly, probably or definitely treatment-related decreased with increased corticosteroid potency, falling from 42% in the taz/plac group, to 36%, 32% and 31% in the tazarotene/low-potency corticosteroid (taz/low), taz/med, and taz/high groups, respectively. (See Table II, below.)

TABLE II

| | Overall incidence of adverse events | | | |
|---|---|---|---|---|
| | Patients (%) | | | |
| | Taz/plac | Taz/low | Taz/med | Taz/high |
| Pruritus | 15 | 19 | 16 | 8 |
| Erythema | 12 | 7 | 6 | 6 |
| Irritation | 8 | 9 | 5 | 4 |
| Burning | 6 | 4 | 4 | 8 |

In view of the above Example, the following conclusions may be drawn. Alternate-day treatment with tazarotene 0.1% gel and the high potency corticosteroid cream was consistently more effective than the other three regimens in reducing plaque elevation, scaling and erythema. Patients in the tazarotene plus high-potency corticosteroid group also achieved significantly higher treatment success rates (≧50% global clinical improvement, and achieved treatment success faster, than patients in the other groups. Treatment-related adverse events comprised mainly mild to moderate local irritation including pruritus, erythema and burning skin. The incidence of treatment-related adverse events decreased as the potency of the corticosteroid cream used increased.

EXAMPLE 2

The study of Example 1 is substantially repeated with fluocinolone acetonide 0.01% cream (low-potency), mometasone furoate 0.1% cream (mid-potency) and fluocinonide 0.05% cream (high-potency) used as the corticosteroids. In this study tazarotene 0.1% gel in combination with a mid-potency or high-potency corticosteroid, when compared with tazarotene plus placebo cream, was associated with significantly higher treatment success rates, significantly greater reductions in scaling, erythema, and overall lesional severity, with a decreased incidence of adverse events. The corticosteroids are Synalar® cream, Elocon® cream and Lidex® cream, respectively.

While particular embodiments of the invention have been described, it will be understood of course that the invention is not limited thereto since many obvious modifications can be made and it is intended to include within this invention any such modifications as will fall within the scope of the appended claims.

Having now described the invention, I claim:

1. A method for treating proliferative skin diseases comprising the administration of an effective amount of a gel comprising about 0.01% to about 2% w/w tazarotene and:
   (a) water;
   (b) edetate disodium;
   (c) ascorbic acid;
   (d) Carbomer 934P;
   (e) Poloxamer 407;
   (f) polyethylene glycol;
   (g) Polysorbate 40;
   (h) hexylene glycol;
   (i) butylated hydroxytoluene;
   (j) butylated hydroxyanisole;
   (k) benzyl alcohol; and
   (l) tromethamine
   and an effective amount of a corticosteroid, wherein said corticosteroid is betamethasone valerate.

2. A method for treating psoriasis in a human subject by topically applying to the psoriatic skin of said subject an effective amount of gel comprising about 0.01% to about 2% w/w tazarotene and:
   (a) water;
   (b) edetate disodium;
   (c) ascorbic acid;
   (d) Carbomer 934P;
   (e) Poloxamer 407;
   (f) polyethylene glycol;
   (g) Polysorbate 40;
   (h) hexylene glycol;
   (i) butylated hydroxytoluene;
   (j) butylated hydroxyanisole;
   (k) benzyl alcohol; and
   (l) tromethamine
   and an effective amount of a corticosteroid wherein said corticosteroid is betamethasone valerate.

3. The method of claim 2 wherein tazarotene is administered once daily in the evening and the corticosteroid is administered once daily in the morning.

4. The method of claim 2 wherein the tazarotene is applied as a 1.0% gel.

5. The method of claim 2 wherein the tazarotene is applied as a 1.0% cream.

6. A method for treating proliferative skin diseases comprising the administration of an effective amount of a gel comprising about 0.01% to about 2% w/w tazarotene and an effective amount of a high potency corticosteroid.

7. The method of claim 6 wherein the gel is a cream.

* * * * *